US008539848B2

(12) United States Patent
Shin et al.

(10) Patent No.: US 8,539,848 B2
(45) Date of Patent: Sep. 24, 2013

(54) SYSTEM FOR EVALUATING CUTTING EFFICIENCY OF ROOT CANAL ROTARY INSTRUMENTS

(75) Inventors: Chow-Shing Shin, Taipei (TW); Zheng-Cheng Lin, Taipei (TW); Chun-Pin Lin, Taipei (TW)

(73) Assignee: National Taiwan University, Taipei (TW)

( * ) Notice: Subject to any disclaimer, the term of this patent is extended or adjusted under 35 U.S.C. 154(b) by 277 days.

(21) Appl. No.: 12/973,833

(22) Filed: Dec. 20, 2010

(65) Prior Publication Data

US 2011/0277567 A1 Nov. 17, 2011

(30) Foreign Application Priority Data

May 13, 2010 (TW) .................. 99115244 A

(51) Int. Cl.
*B23Q 17/09* (2006.01)
*G01M 13/00* (2006.01)
*A61C 5/02* (2006.01)

(52) U.S. Cl.
CPC ............... *G01M 13/00* (2013.01); *A61C 5/023* (2013.01)
USPC ...................... 73/865.9; 73/7; 73/104; 73/866

(58) Field of Classification Search
USPC ................ 73/865.9, 152.01, 85, 7, 104, 866
See application file for complete search history.

(56) References Cited

U.S. PATENT DOCUMENTS 2,572,756 A * 10/1951 Plimmer et al. .............. 29/26 R
5,028,228 A * 7/1991 Ubukata et al. ............... 425/298

OTHER PUBLICATIONS

R. L. Villalobos et al. "A Method to Determine the Cutting Efficiency of Root Canal Instruments in Rotary Motion," Journal of Endodontics, Aug. 1980, vol. 6, p. 667-671, The American Assoication of Endodontists, US.
Edgar Schafer et al., "Comparison of Cutting Efficiency and Instrumentation of Curved Canals with Nickel-Titanium and Stainless-Steel Instruments," Journal of Endodontics, 1999, vol. 25, p. 427-430, The American Assoication of Endodontists, US.
S. Ygues-Henry et al., "Cutting Efficiency Loss of Root Canal Instruments due to Bulk Plastic Deformation, Surface Damage, and Wear," Journal of Endodontics, 1994, vol. 20, p. 367-372, The American Assoication of Endodontists, US.
Seymour Oliet et al., "Cutting Efficiency of Endodontic Reamers," Oral Surg., vol. 36, p. 243-252, The American Assoication of Endodontists, US.
Tung B. Bui et al., "Effect of Electropolishing ProFile Nickel-Titanium Rotary Instruments on Cyclic Fatigue Resistance, Torsional Resistance, and Cutting Efficiency," JOE, Feb. 2008, vol. 34, No. 2, p. 190-193, US.
R. A. Felt., "Flute Design of Endodontic Instruments: Its Influence of Cutting Efficiency," Journal of Endodontics, vol. 8, p. 253-259, The American Assoication of Endodontists, US.

(Continued)

*Primary Examiner* — Hezron E Williams
*Assistant Examiner* — Alexander Mercado

(57) ABSTRACT

A system for evaluating cutting efficiency of root canal rotary instruments is provided. The system includes a root canal rotary instrument, a driving unit, a cutting object, a prestressing force providing unit and a feeding unit. The root canal rotary instrument is attached on the driving unit, and driven thereby. The cutting object is pressed by the prestressing force providing unit to contact the root canal rotary instrument. The feeding unit feeds the cutting object to the root canal rotary instrument, and the root canal rotary instrument cuts an uncut surface of the cutting object.

11 Claims, 7 Drawing Sheets

(56) References Cited

OTHER PUBLICATIONS

S. Yguel-Henry et al., "High Precision, Simulated Cutting Efficiency Measurement of Endodontic Root Canal Instruments: Influence of File Configuration and Lubrication," Journal of Endodontics, Sep. 1990, vol. 16, No. 9, p. 418-422, The American Assoication of Endodontists, US.

Evert Stenman et al., "Machining Efficiency of Endodontic Files: A New Methodology," Journal of Endodontics, Apr. 1990, vol. 16, No. 4, p. 151-157, The American Assoication of Endodontists, US.

Youssef Haikel et al., "Cutting Efficiency of Nickel-Titanium Endodontic Instruments and the Effect of Sodium Hypochlorite Treatment," Journal of Endodontics, Nov. 1998, vol. 24, No. 11, p. 736-739, The American Assoication of Endodontists, US.

Joachim Tepel et al., "Properties of Endodontic Hand Instruments Used in Rotary Motion. Part 1. Cutting Efficiency," Journal of Endodontics, Aug. 1995, vol. 21, No. 8, p. 418-422, The American Assoication of Endodontists, US.

L. R. Ayar et al., "Shaping Ability of ProFile and K3 Rotary Ni-Ti Instruments When Used in a Variable Tip Sequence in Simulated Curved Root Canals," International Endodontics Journal, 2004, vol. 37, p. 593-601, The American Assoication of Endodontists, US.

* cited by examiner

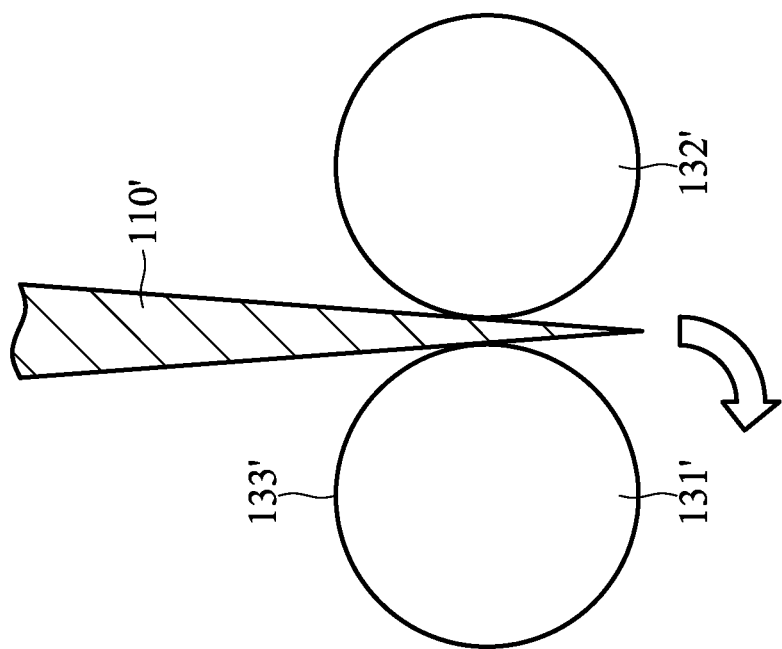

US 8,539,848 B2

SYSTEM FOR EVALUATING CUTTING EFFICIENCY OF ROOT CANAL ROTARY INSTRUMENTS

CROSS REFERENCE TO RELATED APPLICATIONS

This Application claims priority of Taiwan Patent Application No. 099115244, filed on May 13, 2010, the entirety of which is incorporated by reference herein.

BACKGROUND OF THE INVENTION

1. Field of the Invention

The present invention relates to a system for evaluating cutting efficiency of root canal rotary instruments, and in particular relates to a system for evaluating cutting efficiency of root canal rotary instruments with improved evaluating efficiency.

2. Description of the Related Art

Conventionally, two test methods are applied for evaluating cutting efficiency of root canal rotary instruments. In the first test method, a root canal is simulated by teeth or similar material, and the root canal rotary instrument is inserted into the root canal to cut the inner surface of the root canal. In the second test method, two acrylic plates sandwich the root canal rotary instrument, and the root canal rotary instrument cuts the acrylic plates repeatedly. The root canal rotary instrument is cone shaped. The contact position, contact area, contact angle and contact stress between the root canal rotary instrument and the cutting object change with the cutting period and the depth of the groove cut by the root canal rotary instrument. Therefore, though initial test boundary conditions of the different root canal rotary instruments are the same, the test boundary conditions change during the testing process, and cutting efficiency of root canal rotary instruments obtained from conventional test methods is distorted.

BRIEF SUMMARY OF THE INVENTION

A system for evaluating cutting efficiency of root canal rotary instruments is provided. The system includes a root canal rotary instrument, a driving unit, a cutting object, a prestressing force providing unit and a feeding unit. The root canal rotary instrument is attached on the driving unit, and driven thereby. The cutting object is pressed by the prestressing force providing unit to contact the root canal rotary instrument. The feeding unit feeds the cutting object to the root canal rotary instrument, and the root canal rotary instrument cuts an uncut surface of the cutting object.

In the system for evaluating cutting efficiency of root canal rotary instruments of the invention, the rotated cylinders are utilized as the cutting object. The uncut surface of the cutting object is continuously fed to the root canal rotary instrument, and the contact area, contact angle and contact stress between the root canal rotary instrument and the cutting object are not changed with the cutting period and the depth of the groove cut by the root canal rotary instrument. Additionally, by applying the prestressing force, the root canal rotary instrument stably contacts the cutting object. Utilizing the invention, the cutting efficiency of different root canal rotary instruments can be precisely estimated, and the cutting efficiency of different portions of one single root canal rotary instrument can also be obtained.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIG. 7 shows another modified example of the invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
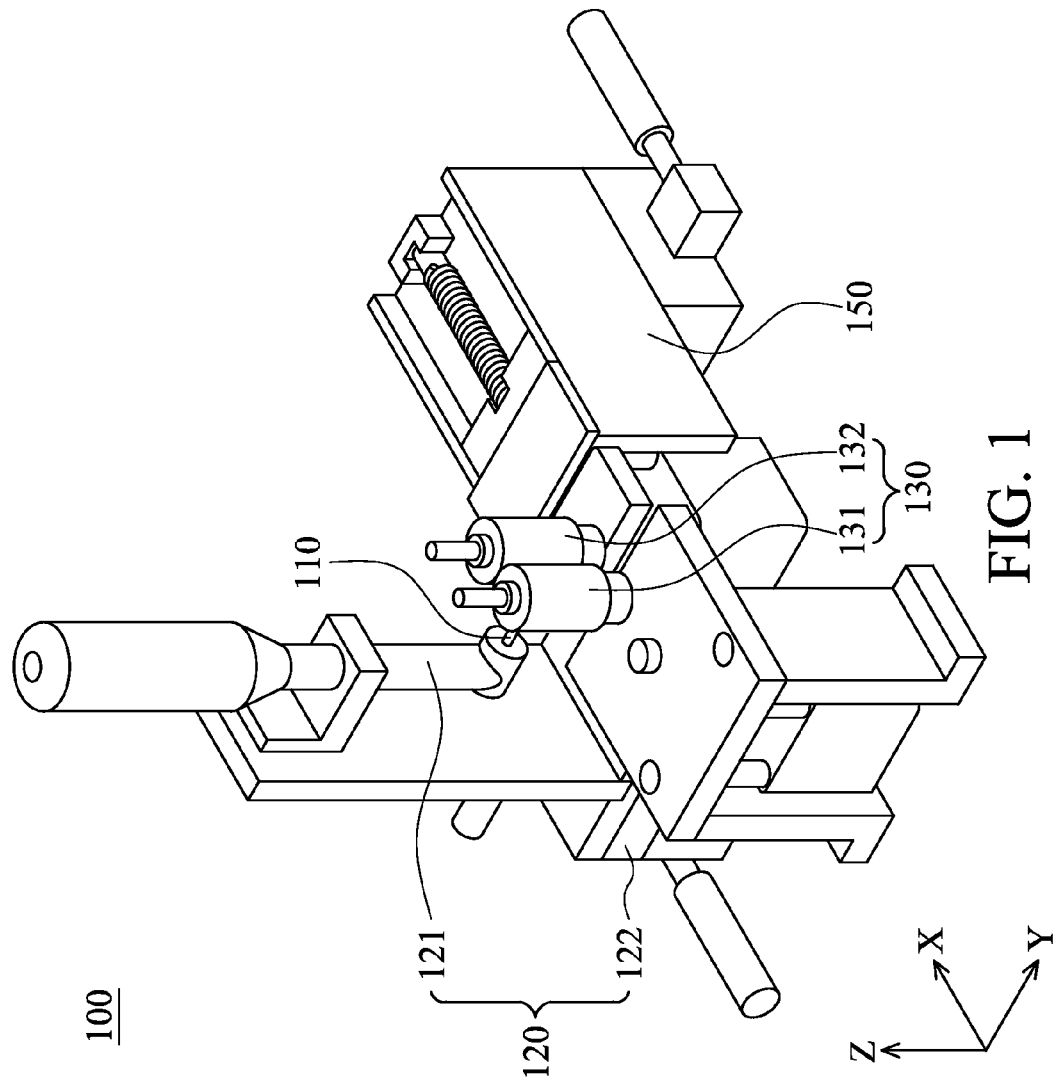
FIG. 1 is a perspective view of a system for evaluating cutting efficiency of root canal rotary instruments of an embodiment of the invention.
Figure 2:
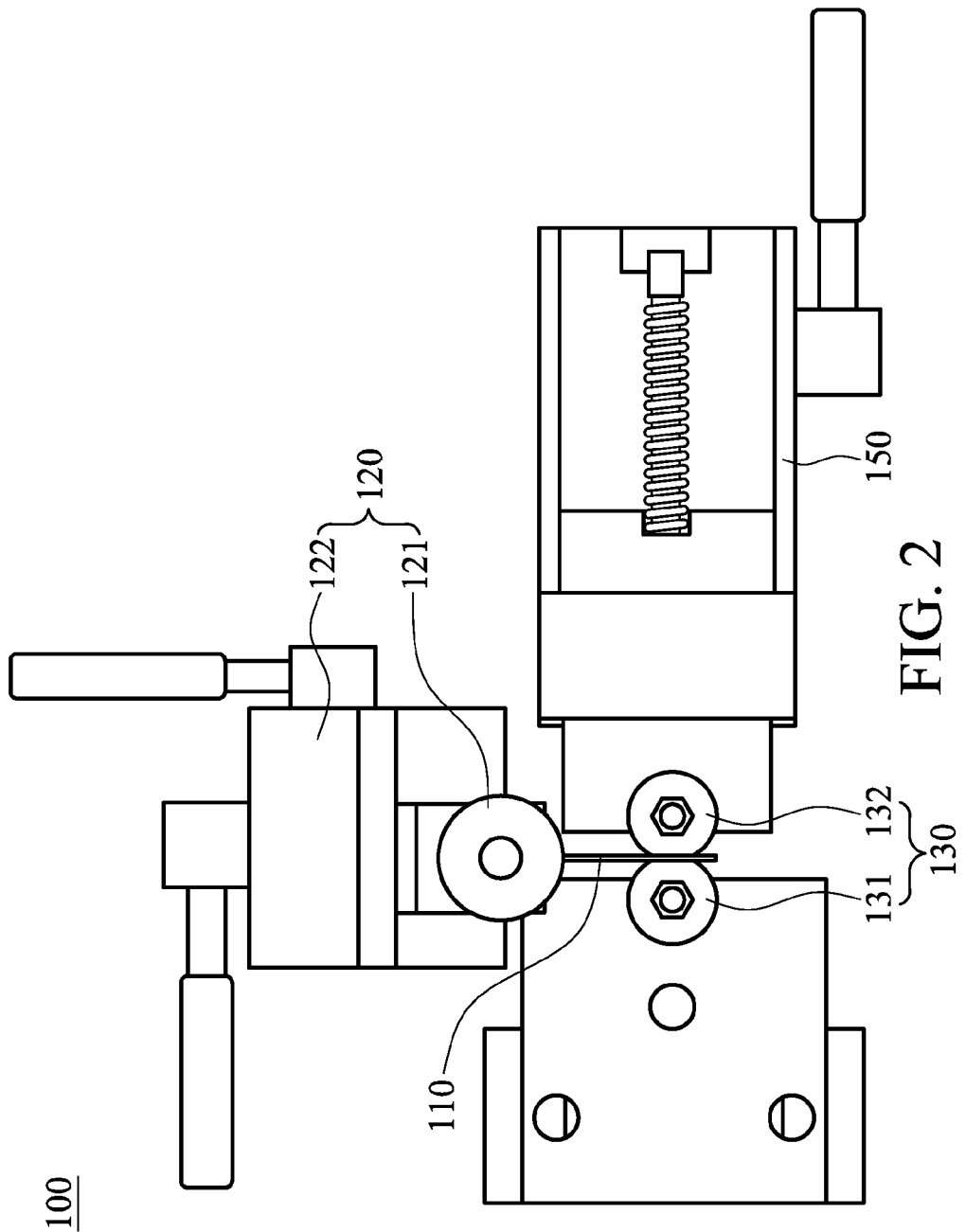
FIG. 2 is a top view of the system for evaluating cutting efficiency of root canal rotary instruments of the embodiment of the invention.

FIG. 1 is a perspective view of a system 100 for evaluating cutting efficiency of root canal rotary instruments of an embodiment of the invention. FIG. 2 is a top view of the system 100 for evaluating cutting efficiency of root canal rotary instruments of the embodiment of the invention. With reference to FIGS. 1 and 2, the system 100 for evaluating cutting efficiency of root canal rotary instruments of the embodiment includes a root canal rotary instrument 110, a driving unit 120, a cutting object 130, a feeding unit 140 (with reference to FIG. 4) and a prestressing force providing unit 150. The root canal rotary instrument 110 is attached on the driving unit 120, and driven thereby. The cutting object 130 is pressed by the prestressing force providing unit 150 to contact the root canal rotary instrument 110. The feeding unit 140 (with reference to FIG. 4) feeds the cutting object 130 to the root canal rotary instrument 110, and the root canal rotary instrument 110 cuts an uncut surface of the cutting object 130.

The driving unit 120 comprises a contra-angle handpiece 121 (or a motor with proper holder) and a first sliding member 122. The root canal rotary instrument 110 is disposed on the contra-angle handpiece 121, and the root canal rotary instrument 110 is driven by the contra-angle handpiece 121. The contra-angle handpiece 121 is disposed on the first sliding member 122, the first sliding member 122 slides in a first direction X and a second direction Z to modify a position of the root canal rotary instrument 110, and the first direction X is perpendicular to the second direction Z.

Figure 3:
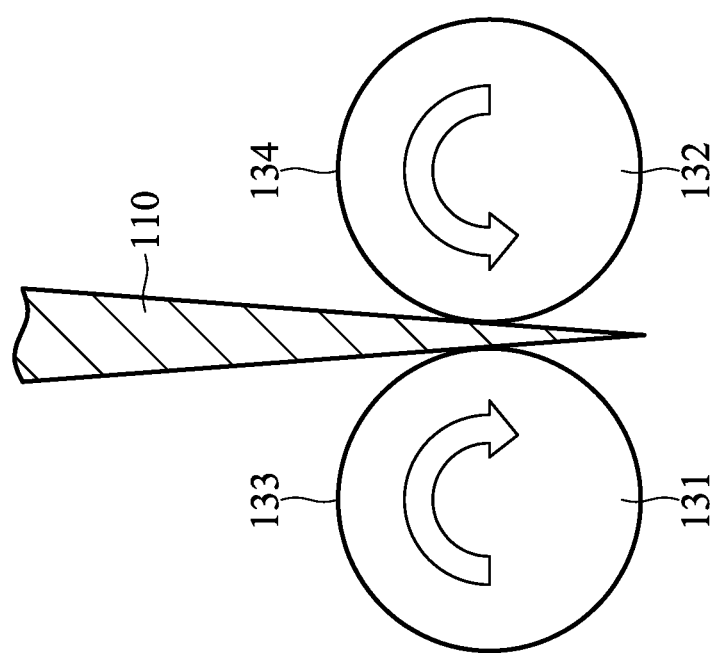
FIG. 3 shows the root canal rotary instrument contacting a first cylinder and a second cylinder.

The cutting object 130 comprises a first cylinder 131 and a second cylinder 132. The cutting object 130 can be made of acrylic. The feeding unit 140 (with reference to FIG. 4) rotates the first cylinder 131 and the second cylinder 132. FIG. 3 shows the root canal rotary instrument 110 contacting the first cylinder 131 and the second cylinder 132. The root canal rotary instrument 110 is located between the first cylinder 131 and the second cylinder 132. The root canal rotary instrument 110 cuts a first periphery surface 133 of the first cylinder 131 and a second periphery surface 134 of the second cylinder 132. The feeding unit 140 (with reference to FIG. 4) rotates the first cylinder 131 and the second cylinder 132 synchronously, and the root canal rotary instrument 110 continuously cuts the uncut portion of the first periphery surface 133 and the second periphery surface 134. In this embodiment, the rotation angles of the first cylinder 131 and the second cylinder 132 are not greater than 360°.

Figure 4:
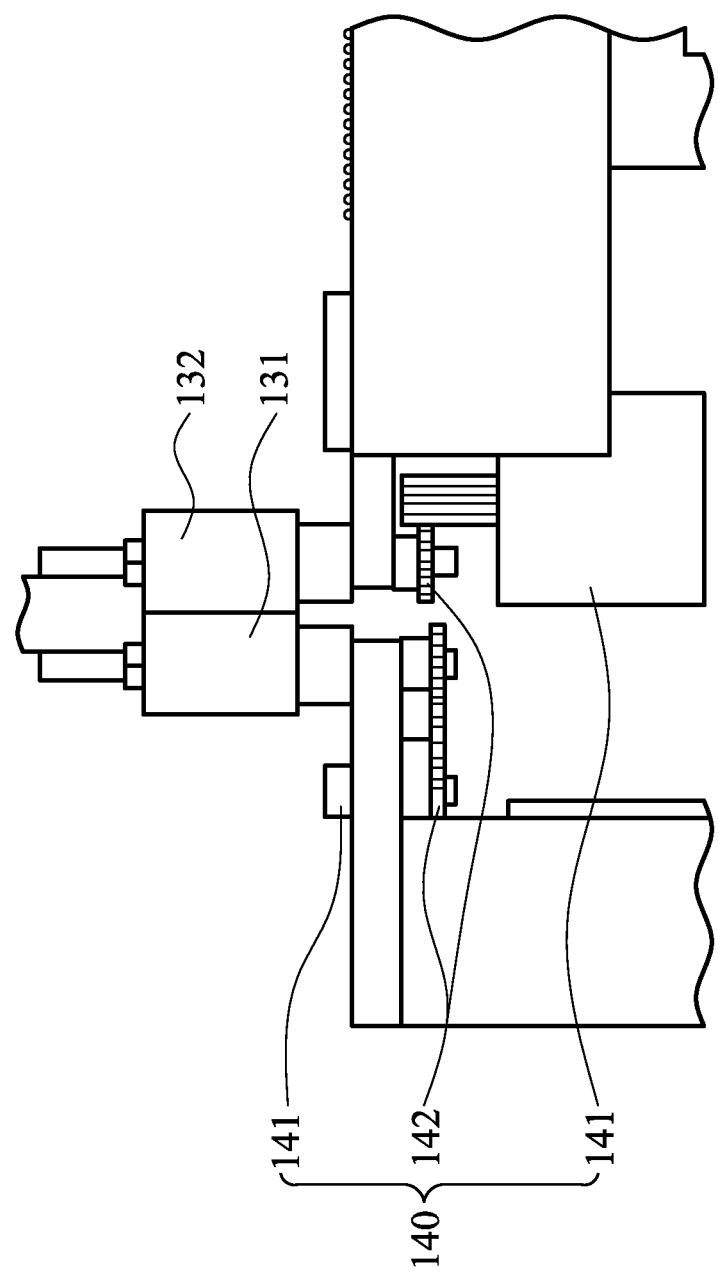
FIG. 4 shows an embodiment of the feeding unit.

FIG. 4 shows an embodiment of the feeding unit 140. The feeding unit 140 comprises a stepper motor 141 and a gear module 142. The stepper motor 141 and the gear module 142 rotate the first cylinder 131 and the second cylinder 132 in opposite directions. The rotation speed of the first cylinder 131 and the second cylinder 132 is 1/40~1/50 round/s. The rotation speed of the first cylinder 131 and the second cylinder 132 can be modified.

Figure 5:
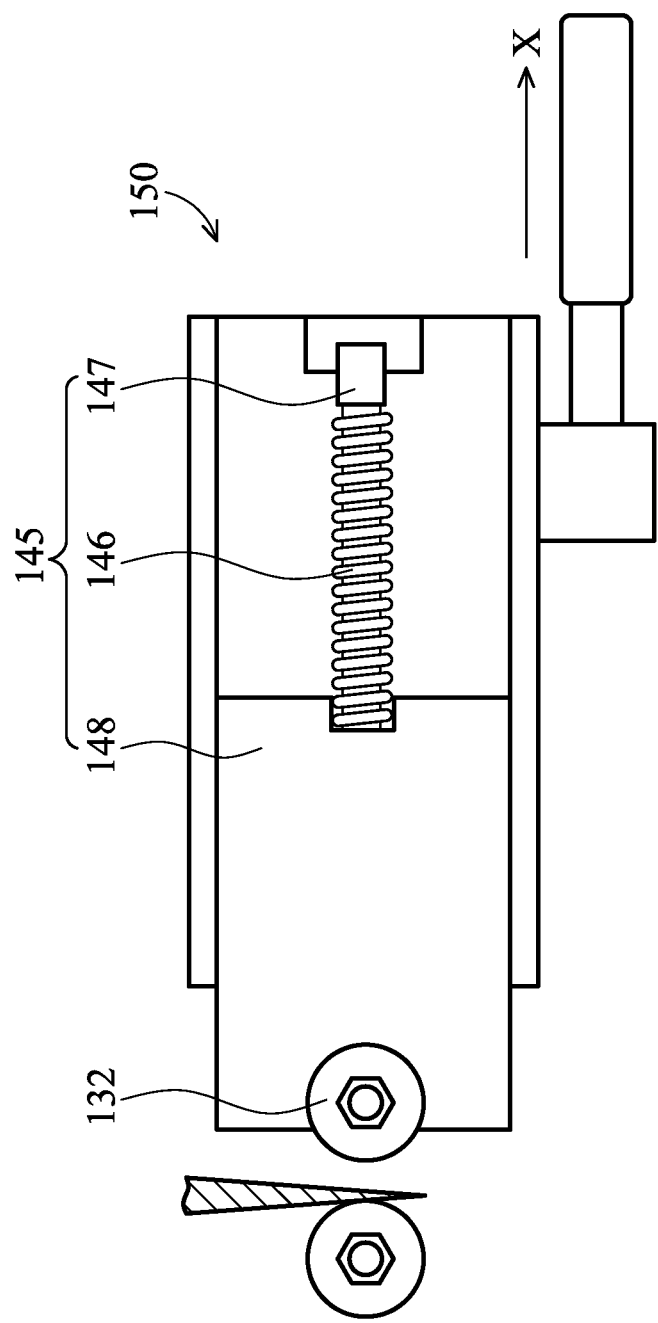
FIG. 5 shows a detailed structure of a second sliding member of the prestressing force providing unit.

FIG. 5 shows a detailed structure of a second sliding member 145 of the prestressing force providing unit 150. The second sliding member 145 slides along the first direction X, and includes a loading element 147, an elastic element 146 and a sliding base 148. The second cylinder 132 is disposed on the sliding base 148. The elastic element 146 pushes the second cylinder 132 contacting the root canal rotary instrument 110, and provides a prestressing force toward the second cylinder 132. The prestressing force is between 5N~10N. The second cylinder 132 therefore sufficiently contacts the root canal rotary instrument 110. The prestressing force can be modified. The elastic element 146 can be spring or other elastic elements.

With reference to FIG. 1, the position of the root canal rotary instrument 110 on a third direction Y can be modified by changing the location of the contra-angle handpiece 121. The portion of the cutting object cut by the root canal rotary instrument 110 can thus be changed.

Cutting efficiency of the root canal rotary instrument can be evaluated by measuring weight variation of the cutting object In the system for evaluating cutting efficiency of root canal rotary instruments of the invention, the rotated cylinders are utilized as the cutting object. The uncut surface of the cutting object is continuously fed to the root canal rotary instrument, and the contact area, contact angle and contact stress between the root canal rotary instrument and the cutting object are not changed with the cutting period and the depth of the groove cut by the root canal rotary instrument. Additionally, by applying the prestressing force, the root canal rotary instrument stably contacts the cutting object. Utilizing the invention, the cutting efficiency of different root canal rotary instruments can be precisely estimated, and the cutting efficiency of different portions of one single root canal rotary instrument can also be obtained.

Figure 6:
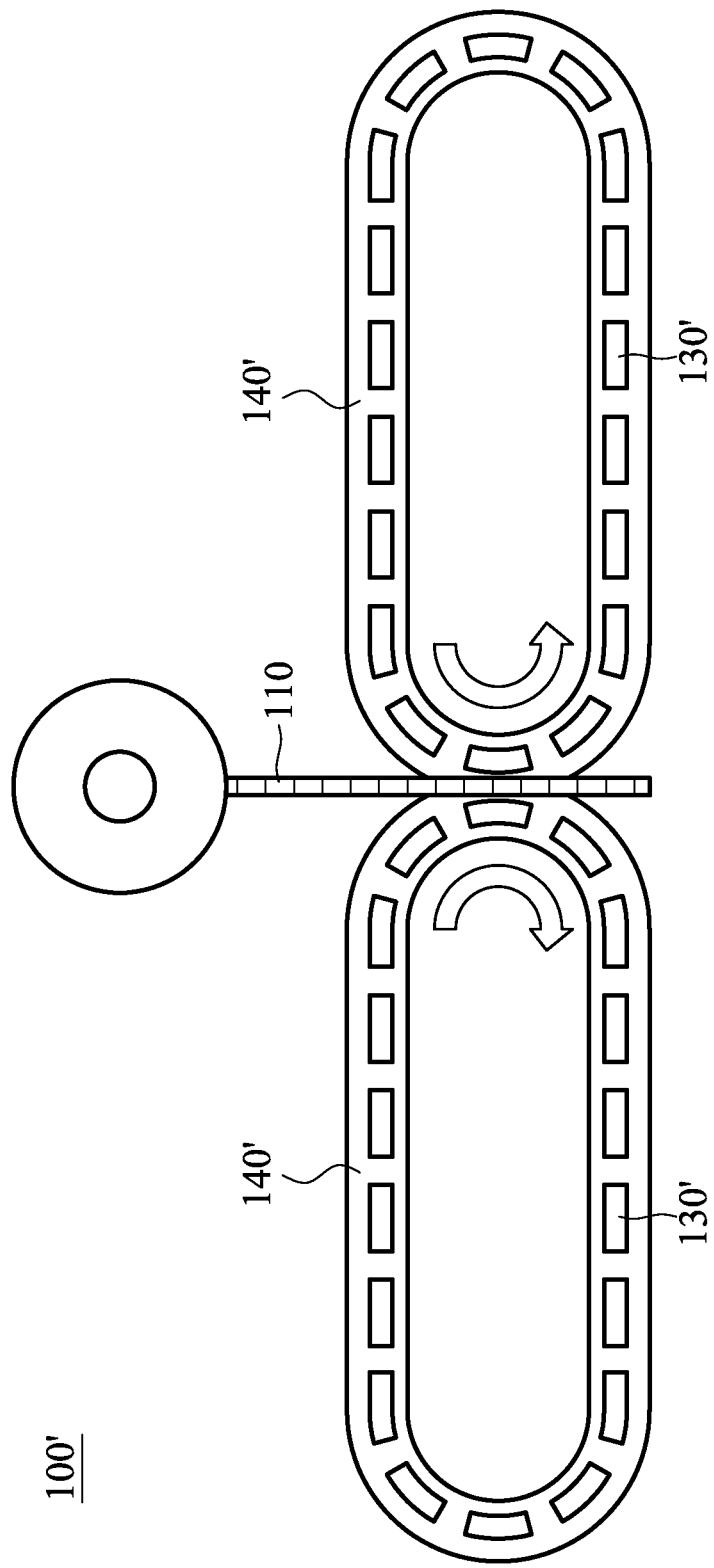
FIG. 6 shows a system for evaluating cutting efficiency of root canal rotary instruments of a modified example of the invention.

FIG. 6 shows a system 100' for evaluating cutting efficiency of root canal rotary instruments of a modified example of the invention, wherein the feeding unit 140' comprises a transporting belt. The feeding unit 140' feeds the cutting object 130' to the root canal rotary instrument 110. The design of the feeding unit of the invention can be modified, and the embodiments above do not limit the invention.

FIG. 7 shows another modified example of the invention, wherein the root canal rotary instrument 110' and the second cylinder 132' are rotated around the first cylinder 131', and the root canal rotary instrument 110' continuously cuts the uncut portion of the first periphery surface 133' of the first cylinder 131'.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A system for evaluating cutting efficiency of root canal rotary instruments, comprising:
a root canal rotary instrument;
a driving unit, wherein the root canal rotary instrument is attached on the driving unit, and driven thereby;
a cutting object;
a prestressing force providing unit, wherein the cutting object is pressed by the prestressing force providing unit to contact the root canal rotary instrument; and
a feeding unit arranged to feed the cutting object to the root canal rotary instrument, such that the root canal rotary instrument cuts an uncut surface of the cutting object,
wherein the driving unit comprises a contra-angle handpiece, the root canal rotary instrument is disposed on the contra-angle handpiece, and the root canal rotary instrument is driven by the contra-angle handpiece,
wherein the driving unit further comprises a first sliding member, the contra-angle handpiece is disposed on the first sliding member, the first sliding member slides in a first direction and a second direction to modify a position of the root canal rotary instrument, and the first direction is perpendicular to the second direction,
wherein the cutting object comprises a first cylinder, and the feeding unit rotates the first cylinder.

2. The system for evaluating cutting efficiency of root canal rotary instruments as claimed in claim 1, arranged such that the root canal rotary instrument cuts a first periphery surface of the first cylinder, the feeding unit rotates the first cylinder, and the root canal rotary instrument continuously cuts the uncut portion of the first periphery surface.

3. The system for evaluating cutting efficiency of root canal rotary instruments as claimed in claim 2, wherein the cutting object comprises a second cylinder, the feeding unit rotates the second cylinder, and the root canal rotary instrument is located between the first cylinder and the second cylinder, arranged such that the root canal rotary instrument cuts a second periphery surface of the second cylinder, the feeding unit rotates the second cylinder, and the root canal rotary instrument continuously cuts the uncut portion of the second periphery surface.

4. The system for evaluating cutting efficiency of root canal rotary instruments as claimed in claim 3, wherein the first cylinder and the second cylinder are rotated respectively in opposite directions.

5. The system for evaluating cutting efficiency of root canal rotary instruments as claimed in claim 4, wherein the first cylinder and the second cylinder are rotated with a speed of 1/40~1/50 rounds.

6. The system for evaluating cutting efficiency of root canal rotary instruments as claimed in claim 3, wherein the prestressing force providing unit further comprises a second sliding member, the second cylinder is disposed on the second sliding member, the second sliding member slides in the first direction, and the second sliding member pushes the second cylinder contacting the root canal rotary instrument.

7. The system for evaluating cutting efficiency of root canal rotary instruments as claimed in claim 6, wherein the second sliding member comprises an elastic element, and the elastic element pushes the second cylinder contacting the root canal rotary instrument.

8. The system for evaluating cutting efficiency of root canal rotary instruments as claimed in claim 7, wherein the elastic element is spring, the elastic element provides a prestressing force toward the second cylinder, and the prestressing force is between 5N~10N.

9. A method for evaluating cutting efficiency of root canal rotary instruments, comprising:
  providing the system for evaluating cutting efficiency of root canal rotary instruments as claimed in claim 1;
  rotating the root canal rotary instrument;
  feeding the cutting object by the feeding unit toward the root canal rotary instrument to be cut thereby; and
  evaluating cutting efficiency of the root canal rotary instrument by measuring weight variation of the cutting object.

10. The method for evaluating cutting efficiency of root canal rotary instruments as claimed in claim 9, further comprising modifying a position of the root canal rotary instrument in a second direction to change contact position of the root canal rotary instrument on the cutting object.

11. The system for evaluating cutting efficiency of root canal rotary instruments as claimed in claim 1, wherein the cutting object is made of acrylic.

* * * * *